United States Patent
Yano et al.

(10) Patent No.: US 7,329,544 B2
(45) Date of Patent: Feb. 12, 2008

(54) PLANT LESION FORMATION SUPPRESSING GENE, SP17 AND USE THEREOF

(75) Inventors: Masahiro Yano, Tsukuba (JP); Utako Yamanouchi, Tsukuba (JP)

(73) Assignees: National Institute of Agrobiological Sciences, Ibaraki (JP); Society for Techno-Innovation of Agriculture, Forestry and Fisheries, Tokyo (JP)

( * ) Notice: Subject to any disclaimer, the term of this patent is extended or adjusted under 35 U.S.C. 154(b) by 756 days.

(21) Appl. No.: 10/168,273

(22) PCT Filed: Oct. 18, 2001

(86) PCT No.: PCT/JP01/09153

§ 371 (c)(1), (2), (4) Date: Oct. 28, 2002

(87) PCT Pub. No.: WO02/33092

PCT Pub. Date: Apr. 25, 2002

(65) Prior Publication Data

US 2004/0058324 A1    Mar. 25, 2004

(30) Foreign Application Priority Data

Oct. 18, 2000    (JP)  ............................. 2000-318557

(51) Int. Cl.
C12N 5/04    (2006.01)
C12N 15/82    (2006.01)
C07H 21/04    (2006.01)

(52) U.S. Cl. .................. 435/419; 435/468; 435/320.1; 536/23.6

(58) Field of Classification Search ..................... None
See application file for complete search history.

(56) References Cited

FOREIGN PATENT DOCUMENTS

| JP | 11-346783 | | 12/1999 |
|---|---|---|---|
| JP | 2000-125885 | | 5/2000 |
| WO | WO 00/53724 | | 9/2000 |
| WO | WO 03/000898 | * | 6/2001 |
| WO | WO 01/70929 A2 | | 9/2001 |

OTHER PUBLICATIONS

Prandl et al. 1998, Mol. Gen. Genet. 258:269-278.*
Molina et al. 1999, Plant J. 17:667-678.*
Fourgoux-Nicol et al 1999, Plant Molecular Biology 40 :857-872.*
Falcon-Perez JM et al. 1999, J Biol Chem. 274:23584-90.*
Lazar et al. 1988, Mol. Cell. Biol. 8:1247-1252.*
Hill et al 1998, Biochem. Biophys. Res. Comm. 244:573-577.*
Guo et al. 2004, Proc. Natl. Acad. Sci. USA 101: 9205-9210.*
Saiki, et al. (1985). Science. 230(4732): 1350-1354.
Saiki, et al. (1988). Science. 239(4839): 487-491.
Southern, EM (1975). J. Mol. Biol. 98(3):503-517.
Toki, et al. (1992). Plant Physiol. 100:1503-1507.
Toki (1997). Plant Molecular Biology Reporter 15(1):16-21.
Altschul, et al. (1990). J. Mol. Biol. 215(3):403-410.
Christou, et al. (1991). Bio/Technology, 9:957-962.
Fuse, et al. (1993). Physiol. Plant.26(1):799-804.
Garliardi, et al. (1995). Plant Mol. Biol. 29(4): 841-856.
Hanahan, et al. (1983). J. Mol. Biol. 166(4):557-580.
Hiei, et al. (1994). Plant J. 6(2):271-282.
Hubel, et al. (1994). Plant Mol. Biol. 26(1):353-362.
Karlin, et al. (1990). Proc. Natl. Acad. Sci. USA. 87(6):2264-2268.
Karlin, et al. (1993). Proc. Natl. Acad. Sci. USA. 90(12):5873-5877.
Kawasaki, et al. (1997). Saibou Kougaku Bessatsu: 124-130. (Submitted with an English Explanation).
Kramer, et al. (1987). Mthods Enzymol. 154: 350-367.
Mandel, et al. (1970). J. Mol. Biol. 53(1):159-162.
Datta (1995). Gene Transfer to Plants: 66-74.
Prandl, et al. (1998). Mol. Gen. Genet. 258(3):269-78.
Queitsch, et al. (2000). Plant Cell 12(4): 479-492.
Rice Genetics Newsletter (1995). 12:54-55.
Scharf, et al. (1993). Plant Physiol. 102(4):1355-1356.
Fuse, et al. (1993). Physiol. Plant. 89(4):799-804.
Database EMBL, Accession No. AC073405, Jun. 28, 2000 (the whole document).
Database EMBL, Accession No. AC027661, Apr. 3, 2000 (the whole document).
Supplementary European Search Report for EP 01 97 6740, mailing date: Jul. 23, 2004.
GENBANK Accession No. U13949, 3 pgs. (Jun. 6, 1995).

* cited by examiner

*Primary Examiner*—Ashwin Mehta
*Assistant Examiner*—Li Zheng
(74) *Attorney, Agent, or Firm*—Ingrid A. Beattie; Cynthia A. Kozakiewicz; Mintz Levin

(57) ABSTRACT

The present inventors successfully isolated a lesion formation suppressing gene (Spl7) from rice via a linkage analysis. It was revealed that introduction of this gene into plants enhances their heat stress resistance and that lesion formation can be suppressed.

7 Claims, 7 Drawing Sheets

SEQUENCE LISTING

```
<160> NUMBER OF SEQ ID NOS: 12

<210> SEQ ID NO 1
<211> LENGTH: 5579
<212> TYPE: DNA
<213> ORGANISM: Oryza sativa
<220> FEATURE:
<223> OTHER INFORMATION: genomic DNA
<220> FEATURE:
<221> NAME/KEY: CDS
<222> LOCATION: (3711)..(3947)
<220> FEATURE:
<221> NAME/KEY: CDS
<222> LOCATION: (4185)..(5327)

<400> SEQUENCE: 1
ttcgaagtcc tgagattagc cgatgagagt tatcaagtcg tcagttgtcg gattctttct      60
atattcagtt aaggaaattg atctactaaa ggaagcttat acagaagaga ccgagttcaa     120
agagaatgcg gcatggaaag ttatctatta attaggaata gtttgttagt ttctttttat     180
ctttaggaaa gtgtgtttag tgttctataa gaactttatc ttttccttt atctttagaa     240 aagtttcttt cttgtctaac aaggacttgt atcaacccat gggtataaat atgtacaccc     300
ggggtctatg taatctatct tcatgatcaa tacaattcag cgcatcgcca ccttttacct     360
tttctacttt attttatcgt ccggcggaac ttggcacctg acacgggct gcatcggtgt     420 tcgatctccg gctaagggt aagtccaatg ttccgccggc caggcaattg tatcgtttac     480
gtcggcgttg ttcaaggctg catcagtaca ttcgacctct tgcattgctc tagtttggat     540
gatatatttg cctacctatt tatcatatgt ctctgttaat ctagttttag catatcaatt     600
tagctctatc ggctgcttct cgttttaggg tttctgccgg tatcggctaa atcgtgttgc     660
tagattagat tatcttagac atctaccacc ctgaaaactc agtcaatagc ttgattgtct     720
agatatcatg tttctttca tacttagtgc tgcattagtt aagtttgatc tactaagtcg     780
tgcttagaac cataatctct agcctgcttc ttgattgcca attagggttt tatcggggtt     840
tcagccggtg agttatctgg acgttgcatc ggctcataag gattgcacat acatataaat     900
tggatttagc cgatgacaac aaaggtttca ctgtttaatc taatcttgtg gatttcatga     960
```

-continued

```
catcggacct ccagccgatg tatgctttaa ccttcggatt aatgctaatt ctatcatatc    1020
aatgctagcc gattggtttc tactagatta tattctata ttacatcatc atcagccgat    1080
tgcctttata tcattatcta cattggacat atagccgatt gtttaaaccc tatcgctatc    1140
cgctgttatc ggcatcggct attatcggct atcggctgga actactccat cagcttgtca    1200
gccgatcggc tgtttatct attatttgca tattttgtca gttgcaggat caaactgact    1260
ggcacgcccg catctcacca acctttggac ctgcactgga gttaagcaga tctcccaggc    1320
cggtgtgttc gattttttca tcaacactac catcttacct accatcaaca cataaaacga    1380
gaagttttat tcctgcaata ccctttacc tacctatcac tcttattact tttttcaatg    1440
attaaggata ttttagtcat tctcactatc tattaattcc accttcggat gctaagaatg    1500 gatttttgt gtgacggagg gagtagttgg gacctaatgt tcggcgtacg taaaacggag    1560
cgactcatta gcacatgatt aattaagtat tatctttttt ataaatagat taatatgatt    1620
ttttaaagca actttcgtat tttttaaaaa aaataaaccg tttagtagtt tgaaaaacgt    1680
gcatgcggaa aaacgagaga gatgagttgg gaaaagtaat agacgaacaa aacctagtag    1740
tacaagctac taccccatt atcaatatte ataagtaaaa tttagagaaa atctaaaaaa    1800
tatcttgaca aacgtccaac cttaagaaat gtcattgatg agtgcgagtt ccaaaaatac    1860
tctcgtataa acgactttat cccagaaatg ctattatcgt taggattcac cttattccgt    1920
gatgttaaat aaagtttcca tcctatacca cttaacggag gggttgctaa cagaaccctc    1980
cttagcaacc ataacgatga cagtattttt aggacaaagt cacatgtata atagtatttc    2040
atgaaacttg ctcttgtcga tggtattttt ttaaattcgg cgctcatcaa taatattcgt    2100
tggaccttct ttaaaattta ttatatctta ggacagaaaa actagtactt cgtcccataa    2160
tataagtgat tttgagtttt tgcttgtact gtttgaccac tcgtcttatt caaagaattt    2220
gtgcaaatat aaaaaacgaa aagttgtgct taaagtactt tagataataa agtaagtcaa    2280
aaaagataaa taataatttt aaattttttt aataagacga ttggtcaaac agtgcaaata    2340
aaaactcaag atcccttata ttatgggata aatggagtac tactccctcc gtcccaaaat    2400
aagtgcagct atagttttcc atgcccaact ttgaccactc atcttatttg aaaaaaatta    2460
aaaacataag tcacaagtaa agtagtattc atgttttatc atcttataac aacaaaattg    2520
ctaattataa aaaaaaatta aataagacgg acgatcaaaa ttgggtgctg aaactcatgg    2580
ctgcacttat tttgggacga aggtagtagt agcttttgat aggtaccagg tactaacgtt    2640
attaattact tagtactact atgagttaac tatggccatg gaaaaagcat gcaggaaaac    2700
acgcacagta tcccgaaatc ctgttgcggt atttgaatgg ttgaatcaaa tactaccagt    2760
accggtctga tgccagcctg ccagccaggc acaccagcga cgatcgattc cggtcggacc    2820
ggaccaccac cggtgtacca ctgtcgcgcc gggcggccgc gccgagcgaa ccgcgcgctg    2880
cgctgccggt ccatttctag aagccctcgc gctcctgatt gcgctctctc tctctctctc    2940
tctctctctc gttcgttccc cggtcagtca accgtctcac gcagcgacca aacgccccgg    3000
agagaggaga aatccgcacg ctcgctcgcg ctggcgcgca gcgcacgcct cccgttctct    3060
cctctatatt atcgccgacg cgcgcgcgcc actgcactag cacggctgca cgccctgcac    3120
ccgttgccac caccaccgcc ttctccgccg cgccgcctc tctcgcgtct cccgctcgtg    3180
cagggcgcgc gtcgtcgggc gagctgctgc cgtctccgtg gccgtggctg atcaggtgag    3240
aattgagaaa ggttgtgagt tttcgcgtgg ttgtctggtt gattcgatcg tgccggcgcg    3300
ccttggcatg gcaggcaaga ttgtatcagg agataatgaa aaaacataca ctgggctttc    3360
```

-continued

| | |
|---|---|
| tttttcttaa tttctttgca ttctttgctt cgacggctat ggttgcttga actgttcagg | 3420 |
| cggcgccttt gtgtatacac gtgcttgtat gtgatgctct ggtcatttct ttttgcagaa | 3480 |
| ctagttggcg ttcgatcgga aagtcgctgt cttttggcga ctcggtgaga atttgcgccg | 3540 |
| cggttcaatg tgaaaaattt tggcccgtgg cgagttggat ttggcgccga gtccattcag | 3600 |
| gtggttaaga cttgttcgtg ggagagcgaa gctgcgcgcg ttaagaccgg gctccgttct | 3660 |
| tgcatcgtgc agagcagctg ctggtttgag aattgagagg cgcggttgac atg gag | 3716 |
|                                                                                                                       Met Glu<br>                                                                                                                       1 | |
| agt tcc aac ctg ggc ggc ggc ggc gga ggc ggc ggc ggt ggg ccg<br>Ser Ser Asn Leu Gly Gly Gly Gly Gly Gly Gly Gly Gly Gly Pro<br>         5                   10                  15 | 3764 |
| ccg ccg ttc ttg atc aag acg tac gag atg gtg gag gac gcg gcg acc<br>Pro Pro Phe Leu Ile Lys Thr Tyr Glu Met Val Glu Asp Ala Ala Thr<br>    20                       25                      30 | 3812 |
| aac cac gtc gtg tcg tgg ggc ccc ggc ggc gcc agc ttc gtc gtg tgg<br>Asn His Val Val Ser Trp Gly Pro Gly Gly Ala Ser Phe Val Val Trp<br>35                     40                      45                  50 | 3860 |
| aac ccg ctc gac ttc tcc cgt gac ctg ttg ccc aag tac ttc aag cac<br>Asn Pro Leu Asp Phe Ser Arg Asp Leu Leu Pro Lys Tyr Phe Lys His<br>                  55                      60                      65 | 3908 |
| aac aac ttc tcc agc ttc atc agg cag ctc aac acc tac gtgagtcaca<br>Asn Asn Phe Ser Ser Phe Ile Arg Gln Leu Asn Thr Tyr<br>           70                      75 | 3957 |
| aacacaatcc cctttgcttc ttgaaacgaa acaaacattg caacaatcat gtgctactgt | 4017 |
| ttgcttgtaa attagtagtt ccttgttctt ggtttgtttg gatgatttta ccattgacac | 4077 |
| agcagccggt tttatatagc ctatttgatt ttctgtaaaa tagttcttta ttcttggttg | 4137 |
| gtttgaccgt agctgaattt tgacttcaat tggcatcttc ctttcag ggt ttc cga<br>                                                                                    Gly Phe Arg<br>                                                                                    80 | 4193 |
| aaa atc gat cct gag aga tgg gag ttc gca aac gag gat ttc ata aga<br>Lys Ile Asp Pro Glu Arg Trp Glu Phe Ala Asn Glu Asp Phe Ile Arg<br>                85                      90                      95 | 4241 |
| ggg cac acg cac ctt ctg aag aac atc cat cga cgc aag ccc gtg cac<br>Gly His Thr His Leu Leu Lys Asn Ile His Arg Arg Lys Pro Val His<br>100                     105                      110 | 4289 |
| agc cac tcc ctc cag aac cag ata aac gga cca ctc gcc gaa tcg gag<br>Ser His Ser Leu Gln Asn Gln Ile Asn Gly Pro Leu Ala Glu Ser Glu<br>115                   120                   125                   130 | 4337 |
| agg cgc gag ctc gaa gaa gag atc aac cgg ctc aag tac gag aag agc<br>Arg Arg Glu Leu Glu Glu Glu Ile Asn Arg Leu Lys Tyr Glu Lys Ser<br>                    135                      140                      145 | 4385 |
| atc ctc gtc gcg gac ctc cag agg cag aac cag cag cag tac gtg atc<br>Ile Leu Val Ala Asp Leu Gln Arg Gln Asn Gln Gln Gln Tyr Val Ile<br>                150                      155                      160 | 4433 |
| aac tgg cag atg cag gcg atg gaa ggc agg cta gtg gcg atg gag caa<br>Asn Trp Gln Met Gln Ala Met Glu Gly Arg Leu Val Ala Met Glu Gln<br>                  165                   170                   175 | 4481 |
| cgg cag aag aac atc gtg gcc tcc ctg tgc gag atg ctg cag aga cgc<br>Arg Gln Lys Asn Ile Val Ala Ser Leu Cys Glu Met Leu Gln Arg Arg<br>180                     185                   190 | 4529 |
| ggt ggc gcc gtg tcg agc tcg ctg ctg gag tcc gac cat ttc agc aag<br>Gly Gly Ala Val Ser Ser Ser Leu Leu Glu Ser Asp His Phe Ser Lys<br>195                   200                   205                   210 | 4577 |
| aag agg agg gtc ccg aag atg gat ctc ttc gtc gac gat tgc gcg gcg<br>Lys Arg Arg Val Pro Lys Met Asp Leu Phe Val Asp Asp Cys Ala Ala | 4625 |

```
                  215                 220                 225
ggc gaa gaa cag aag gtg ttc cag ttc cag gga att ggg acg gat gca      4673
Gly Glu Glu Gln Lys Val Phe Gln Phe Gln Gly Ile Gly Thr Asp Ala
            230                 235                 240 ccg gcc atg cct ccc gtg ctt cct gtg acc aat ggt gag gct ttt gac      4721
Pro Ala Met Pro Pro Val Leu Pro Val Thr Asn Gly Glu Ala Phe Asp
        245                 250                 255 agg gtt gag ctg agc ctg gtc tcc ctg gag aaa ctc ttc cag aga gca      4769
Arg Val Glu Leu Ser Leu Val Ser Leu Glu Lys Leu Phe Gln Arg Ala
    260                 265                 270 aat gat gct tgc aca gct gct gaa gaa atg tac tcc cat ggt cat ggt      4817
Asn Asp Ala Cys Thr Ala Ala Glu Glu Met Tyr Ser His Gly His Gly
275                 280                 285                 290 ggt act gaa ccc agc act gct ata tgt cct gaa gag atg aac act gca      4865
Gly Thr Glu Pro Ser Thr Ala Ile Cys Pro Glu Glu Met Asn Thr Ala
                295                 300                 305 cca atg gag aca ggc atc gat ctt cag tta cca gct agc ctc cat ccc      4913
Pro Met Glu Thr Gly Ile Asp Leu Gln Leu Pro Ala Ser Leu His Pro
            310                 315                 320 agc tca ccc aac aca ggg aat gcc cat ctc cat tta tcc act gaa ctc      4961
Ser Ser Pro Asn Thr Gly Asn Ala His Leu His Leu Ser Thr Glu Leu
        325                 330                 335 aca gag tct cca ggt ttt gtg cag agt cca gag ctg cca atg gca gag      5009
Thr Glu Ser Pro Gly Phe Val Gln Ser Pro Glu Leu Pro Met Ala Glu
    340                 345                 350 att cgt gaa gat atc cat gtg aca aga tac cca aca caa gct gat gta      5057
Ile Arg Glu Asp Ile His Val Thr Arg Tyr Pro Thr Gln Ala Asp Val
355                 360                 365                 370 aat tct gag att gcc tcc tcc act gat act tca caa gat ggc acg tca      5105
Asn Ser Glu Ile Ala Ser Ser Thr Asp Thr Ser Gln Asp Gly Thr Ser
                375                 380                 385 gaa act gaa gct tcg cat gga ccg acc aac gat gtg ttt tgg gag cgg      5153
Glu Thr Glu Ala Ser His Gly Pro Thr Asn Asp Val Phe Trp Glu Arg
            390                 395                 400 ttc ctc aca gag act cca cgg tca tgt ttg gat gag tca gaa aga caa      5201
Phe Leu Thr Glu Thr Pro Arg Ser Cys Leu Asp Glu Ser Glu Arg Gln
        405                 410                 415 gag tct ccc aag gac gat gta aaa gca gaa tta ggc tgc aat ggc ttc      5249
Glu Ser Pro Lys Asp Asp Val Lys Ala Glu Leu Gly Cys Asn Gly Phe
    420                 425                 430 cat cac cgg gag aag gtt gat cag atc acc gag caa atg ggg cac ctt      5297
His His Arg Glu Lys Val Asp Gln Ile Thr Glu Gln Met Gly His Leu
435                 440                 445                 450 gct tca gcc gag cag act ctg cat acc tga tgcagtaata ccatttgcgc        5347
Ala Ser Ala Glu Gln Thr Leu His Thr
                455 ggattcatag ttcgtgtgta aattagcgaa gatgtaaatt atagcttaga tcggattaga    5407 ggcttgcgtg ttactttaca gatttcaacc ttttattaga ttacaatagg tctttcacaa    5467 tttatgattc tgttctatcc gctgactact gtgcataaat ttttttagt agaccatatc     5527 cattttgta ctccattgcc cttctaagat tcctcgttaa aatctcagat ct             5579

<210> SEQ ID NO 2
<211> LENGTH: 459
<212> TYPE: PRT
<213> ORGANISM: Oryza sativa

<400> SEQUENCE: 2

Met Glu Ser Ser Asn Leu Gly Gly Gly Gly Gly Gly Gly Gly Gly Gly
```

-continued

```
1               5                   10                  15
Gly Pro Pro Phe Leu Ile Lys Thr Tyr Glu Met Val Glu Asp Ala
            20                  25                  30
Ala Thr Asn His Val Val Ser Trp Gly Pro Gly Ala Ser Phe Val
            35                  40                  45
Val Trp Asn Pro Leu Asp Phe Ser Arg Asp Leu Leu Pro Lys Tyr Phe
 50                  55                  60
Lys His Asn Asn Phe Ser Ser Phe Ile Arg Gln Leu Asn Thr Tyr Gly
 65                  70                  75                  80
Phe Arg Lys Ile Asp Pro Glu Arg Trp Glu Phe Ala Asn Glu Asp Phe
                    85                  90                  95
Ile Arg Gly His Thr His Leu Leu Lys Asn Ile His Arg Arg Lys Pro
                100                 105                 110
Val His Ser His Ser Leu Gln Asn Gln Ile Asn Gly Pro Leu Ala Glu
                115                 120                 125
Ser Glu Arg Arg Glu Leu Glu Glu Ile Asn Arg Leu Lys Tyr Glu
    130                 135                 140
Lys Ser Ile Leu Val Ala Asp Leu Gln Arg Gln Asn Gln Gln Gln Tyr
145                 150                 155                 160
Val Ile Asn Trp Gln Met Gln Ala Met Glu Gly Arg Leu Val Ala Met
                165                 170                 175
Glu Gln Arg Gln Lys Asn Ile Val Ala Ser Leu Cys Glu Met Leu Gln
                180                 185                 190
Arg Arg Gly Gly Ala Val Ser Ser Leu Leu Glu Ser Asp His Phe
    195                 200                 205
Ser Lys Lys Arg Arg Val Pro Lys Met Asp Leu Phe Val Asp Asp Cys
    210                 215                 220
Ala Ala Gly Glu Glu Gln Lys Val Phe Gln Phe Gln Gly Ile Gly Thr
225                 230                 235                 240
Asp Ala Pro Ala Met Pro Pro Val Leu Pro Val Thr Asn Gly Glu Ala
                245                 250                 255
Phe Asp Arg Val Glu Leu Ser Leu Val Ser Leu Glu Lys Leu Phe Gln
                260                 265                 270
Arg Ala Asn Asp Ala Cys Thr Ala Ala Glu Glu Met Tyr Ser His Gly
    275                 280                 285
His Gly Gly Thr Glu Pro Ser Thr Ala Ile Cys Pro Glu Glu Met Asn
    290                 295                 300
Thr Ala Pro Met Glu Thr Gly Ile Asp Leu Gln Leu Pro Ala Ser Leu
305                 310                 315                 320
His Pro Ser Ser Pro Asn Thr Gly Asn Ala His Leu His Leu Ser Thr
                325                 330                 335
Glu Leu Thr Glu Ser Pro Gly Phe Val Gln Ser Pro Glu Leu Pro Met
                340                 345                 350
Ala Glu Ile Arg Glu Asp Ile His Val Thr Arg Tyr Pro Thr Gln Ala
                355                 360                 365
Asp Val Asn Ser Glu Ile Ala Ser Ser Thr Asp Thr Ser Gln Asp Gly
    370                 375                 380
Thr Ser Glu Thr Glu Ala Ser His Gly Pro Thr Asn Asp Val Phe Trp
385                 390                 395                 400
Glu Arg Phe Leu Thr Glu Thr Pro Arg Ser Cys Leu Asp Glu Ser Glu
                405                 410                 415
Arg Gln Glu Ser Pro Lys Asp Asp Val Lys Ala Glu Leu Gly Cys Asn
    420                 425                 430
```

```
Gly Phe His His Arg Glu Lys Val Asp Gln Ile Thr Glu Gln Met Gly
        435                 440                 445

His Leu Ala Ser Ala Glu Gln Thr Leu His Thr
        450                 455
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 3
gacctgtgct ctgcctttct                                           20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 4
gtatgccaac tgctcaactt                                           20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 5
tctctctcgt tcgttccccg                                           20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 6
tggataaatg gagatgggca                                           20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 7
tcggcatcgg ctattatcgg                                           20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:an

```
            artificially synthesized primer sequence

<400> SEQUENCE: 8
gatttcggga tactgtgcgt                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 9
acgatgtgtt ttgggagcgg                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 10
gacctgtgct ctgcctttct                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 11
gtctccgtgg ccgtggctga                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 12
aacgaggaat cttagaaggg                                              20
```

PLANT LESION FORMATION SUPPRESSING GENE, SP17 AND USE THEREOF

TECHNICAL FIELD

The present invention relates to a gene involved in lesion formation on plants and heat stress resistance in plants, as well as methods of modifying plants via the gene. The present inventions have utility in agriculture fields, including plant-breeding technology.

BACKGROUND ART

Various mutant strains of rice have been produced in the past. These include mutant strains where lesion-like necrotic spots are formed on the leaf in connection with the growth of the rice (FIG. 1)(Rice Genetics Newsletter 12: 9-153 (1995)). This lesion formation occurs in these mutant strains under high temperature and strong light, thereby suggesting a relationship between the mutant genes and avoidance of damage by light or heat (Fuse T. et al., Physiol. Plant 89: 799-804 (1993)). On the other hand, these genes are also postulated to be related to hypersensitivity reaction in plant cells and resulting cell death, because some plants that form lesions become resistant to infections from pathogenic microorganisms (Kawasaki T. and Shimamoto K., Cell Engineering Supplement "Plant Cell Engineering Series 8: Disease Resistance of Plants at Molecular Level" pp. 124-130 (1997)).

Therefore, identification of this mutant gene in these mutant strains along with the isolation of the corresponding wild type gene may enable suppression of lesion formation and an increased resistance to stress, such as light and heat, in rice plant by introducing the gene to arbitrary cultivars via transformation methods.

Hence, there was a need in the art to identify the mutant gene in these mutant strains and also to isolate the corresponding wild type gene.

DISCLOSURE OF THE INVENTION

This need in the art led to the present invention, the object of which is to isolate a novel gene related to suppression of lesion formation on plants. Another object of the present invention is to modify plants by utilizing this novel gene.

In order to accomplish the object to identify the mutant gene and also isolate the corresponding wild type gene, the present inventors conducted extensive research by focusing on Spl7, in which a mutant gene exists on chromosome 5, among mutant strains forming lesion-like necrotic spots on the leaf in connection with the growth of rice.

First, the present inventors conducted linkage analysis and aligned Spl7Spl7 gene region of yeast artificial chromosome (YAC) clones. Specifically, linkage analysis of large segregating population, essential for the isolation of the Spl7Spl7 gene, was conducted. Furthermore, YAC clones existing adjacent to the Spl7Spl7 locus were identified by utilizing the YAC genomic clone library constructed in the Rice Genome Research Program. Then, the end fragments of the identified YAC clones were isolated and aligned to demonstrate that the YAC clones include an Spl7Spl7 gene region (FIG. 2C).

The present inventors selected 9 PAC clones from a Nipponbare genomic PAC clone library, constructed in the Rice Genome Research Program, using STS primer sets prepared from the RFLP marker C11368, a gene on the same locus as the Spl7Spl7 locus. These PAC clones were aligned to indicate the PAC clone containing an Spl7Spl7 locus (FIG. 2D).

According to a fine scale genetic map, constructed using end fragments of YAC and PAC clones aligned in the Spl7Spl7 region as novel RFLP markers or CAPS markers, the Spl7Spl7 locus was demonstrated to exist in a genomic region of about 16 kb between RFLP markers P461H4T and P693G10S (FIG. 2).

The nucleotide sequence of the candidate genomic region was analyzed. Based on the sequence information, a novel CAPS marker was constructed to further delimit the candidate region, and it was concluded that the Spl7 gene existed on a genomic region of about 3 kb between CAPS markers S12C6-6d and HsfC3-3' (FIG. 3).

Gene prediction and similarity search was conducted against the nucleotide sequence of the candidate genomic region. It revealed that there was only one predicted ORF, that has similar sequence with the Hsf gene isolated from plants such as tomato and *Arabidopsis*. Thus, the gene was deemed to be a candidate for the Spl7 gene, and the nucleotide sequence of the corresponding region in a mutant strain KL210 was determined. The result revealed a nucleotide substitution in the nucleotide sequence of the mutant gene when compared with the wild type gene (FIG. 4). An amino acid substitution correlated with the nucleotide substitution was considered to be the cause of the loss or decrease in function of the Spl7 protein.

Furthermore, the present inventors introduced the genomic region (specified as the candidate for the Spl7 gene) into the Spl7 mutant strain by inserting this region into a vector, which can be transformed using *Agrobacterium*. The transformed plants were grown in an isolated growth chamber under natural photoperiod conditions to monitor the formation of lesions. Lesions were observed on both control plants (transformed only with the vector) and mutant strains at the late phase of growth, whereas none of the plants transformed with the candidate gene showed any lesion formation (FIG. 5). Hence it can be concluded that, the candidate gene region suppressed the lesion formation in the mutant strain KL210. Furthermore, in selfed progeny of transgenic plants segregation ratio between plants forming lesions and those that did not form any, was fitted to the expected ratio. Therefore, it was concluded that the candidate gene was the Spl7 gene.

Moreover, the present inventors tested necessary conditions for lesion formation. It was discovered that both high temperature (FIG. 6) and ultraviolet irradiation are conditions that enhance lesion formation (FIG. 7). These facts indicate that the Spl7 gene plays an important role in preventing high-temperature stress in plants. Thus, by breeding transgenic plants expressing the Spl7 gene, it will be possible to enhance the inherent ability of plants to avoid heat stress and to suppress lesion formation on plants.

In other words, the present inventors have succeeded in isolating a gene involved in suppressing lesion formation on plants. The present inventors also found that this gene can suppress lesion formation on plants and that heat stress resistance of plants can be enhanced via this gene as well, thereby completing the present invention.

More specifically, this invention provides the following:

(1) a DNA encoding a protein derived from plants that suppresses the lesion formation on plants, which DNA is selected from the group consisting of:

(a) a DNA encoding a protein comprising the amino acid sequence of SEQ ID NO: 2;

(b) a DNA including the coding region of the nucleotide sequence of SEQ ID NO: 1;

(c) a DNA encoding a protein comprising the amino acid sequence of SEQ ID NO: 2 in which one or more amino acids are substituted, deleted, added and/or inserted; and (d) a DNA capable of hybridizing under stringent conditions with the DNA consisting of the nucleotide sequence of SEQ ID NO: 1;

(2) a DNA encoding a protein derived from plants that enhances the heat stress resistance of plants, wherein said DNA is selected from the group consisting of:

(a) a DNA encoding a protein comprising the amino acid sequence of SEQ ID NO: 2;

(b) a DNA including the coding region of the nucleotide sequence of SEQ ID NO: 1;

(c) a DNA encoding a protein comprising the amino acid sequence of SEQ ID NO: 2 in which one or more amino acids are substituted, deleted, added and/or inserted; and (d) a DNA capable of hybridizing under stringent conditions with the DNA consisting of the nucleotide sequence of SEQ ID NO: 1;

(3) a vector comprising the DNA of (1) or (2);

(4) a transformed cell into which the DNA of (1) or (2), or the vector of (3) has been introduced;

(5) the transformed cell of (4), wherein said transformed cell is a plant cell;

(6) a protein encoded by the DNA of (1) or (2);

(7) a method for producing the protein of (6), wherein said method comprises: cultivating the transformed cell of (4); and collecting an expressed protein from the transformed cell or culture supernatant thereof;

(8) a plant transformant comprising the transformed cell of (5);

(9) a plant transformant which is a progeny or a clone of the plant transformant of (8);

(10) a breeding material of the plant transformant of (8) or (9);

(11) a method for producing the plant transformant of (8), wherein said method comprises:

(a) introducing the DNA of (1) or (2) into a plant cell; and (b) regenerating a plant from said plant cell;

(12) a method for suppressing lesion formation on plants, wherein said method comprises the step of expressing the DNA of (1) in cells of said plant body;

(13) a method for enhancing the heat stress resistance of plants, wherein said method comprises the step of expressing the DNA of (2) in cells of the plant body;

(14) an antibody that binds to the protein of (6); and

(15) a polynucleotide comprising at least 15 nucleotides that are complementary to a DNA consisting of the nucleotide sequence of SEQ ID NO: 1 or a complementary strand thereof.

The present invention provides a DNA encoding a Spl7 protein. Nucleotide sequence of the Spl7 genomic DNA of rice Nipponbare is set forth in SEQ ID NO: 1, and the amino acid sequence of a protein encoded by said DNA is set forth in SEQ ID NO: 2. The Spl7 gene has been known to be involved in suppressing the lesion formation in rice. It exists somewhere within the vast region of chromosome 5. However, the Spl7Spl7 gene had not been previously identified or isolated. After performing extensive research, the present inventors finally identified the region where the gene exists, and were the first to isolate this gene as a single gene.

Spl7 protein has a function to suppress lesion formation on rice caused by heat stress. Furthermore, the relation of Spl7 protein to the transcriptional regulation of heat shock protein genes is suggested from the structure of the Spl7 protein. Recently, one of heat shock proteins was reported to be closely related to the avoidance of heat stress in plants (Queitsch C. et al., Plant Cell 12: 479-492 (2000)). Therefore, it is concluded that heat stress resistance of plants can be enhanced and lesion formation thereby suppressed, by transforming plants with DNA encoding the Spl7 protein.

DNA encoding the Spl7 protein of the present invention includes genomic DNA, cDNA, and chemically synthesized DNA. A genomic DNA and cDNA can be prepared according to conventional methods known to those skilled in the art. More specifically, genomic DNA can be prepared as follows: (1) extract genomic DNA from rice cultivars having Spl7Spl7 gene (e.g., Nipponbare); (2) construct a genomic library (utilizing a vector, such as, plasmid, phage, cosmid, BAC, PAC, etc.); (3) spread the library; and (4) conduct colony hybridization or plaque hybridization using a probe prepared based on the DNA encoding a protein of the present invention (e.g., SEQ ID NO: 1). Alternatively, a genomic DNA can be prepared via PCR using primers specific for a DNA encoding the protein of the present invention (e.g., SEQ ID NO: 1). On the other hand, cDNA can be prepared as follows: (1) synthesize cDNAs based on mRNAs extracted from rice cultivars having the Spl7 gene (e.g., Nipponbare); (2) prepare a cDNA library by inserting the synthesized cDNA into vectors, such as λZAP; (3) spread the cDNA library; and (4) conduct colony hybridization or plaque hybridization as described above. Alternatively, cDNA can be also prepared by PCR.

The present invention includes DNAs encoding proteins (Nipponbare) that are functionally equivalent to the Spl7 protein of SEQ ID NO: 2. Although there is no limitation regarding the plant species from which the DNA of the present invention is derived, they are preferably Gramineae, and most preferably rice. Herein, the phrase "functionally equivalent to the Spl7 protein," as used herein, indicates that the object protein has the function of suppressing lesion formation on plants and/or the function of enhancing heat stress resistance of plants.

Examples of such DNAs include those encoding mutants, derivatives, alleles, variants, and homologues comprising the amino acid sequence of SEQ ID NO: 2 wherein one or more amino acids are substituted, deleted, added and/or inserted.

Examples of methods for preparing a DNA encoding a protein comprising altered amino acids well known to those skilled in the art include the site-directed mutagenesis (Kramer, W. and Fritz, H.-J., "Oligonucleotide-directed construction of mutagenesis via gapped duplex DNA." Methods in Enzymology, 154: 350-367 (1987)). The amino acid sequence of a protein may also be mutated in nature due to a mutation of its corresponding nucleotide sequence. A DNA encoding protein having the amino acid sequence of the natural Spl7 protein where one or more amino acids are substituted, deleted, and/or added are also included within the scope of the DNA of the present invention, provided they encode a protein functionally equivalent to the natural Spl7 protein (SEQ ID NO: 2). Additionally, nucleotide sequence mutants that do not give rise to amino acid sequence changes in the protein (degeneracy mutants) are also included within the scope of the DNA of the present invention.

The present inventors were able to access whether a DNA encoded a protein that suppressed lesion formation on plants by inserting the subject DNA into an appropriate vector, transforming a Spl7 mutant strain therewith, and observing whether the lesion formation on the mutant strain was suppressed or not (described in Example 6). On the other hand, whether a DNA encodes a protein having a function that enhances heat stress resistance of plants or not can be assessed by the following steps: inserting the subject DNA into an appropriate vector; transforming the wild type strain with said vector; observing the growth of the strain under both high temperature conditions (approximately 40° C.) and low temperature conditions (approximately 25° C.); and then comparing the decrease in growth rate of this transformed wild type strain under high temperature with that of the wild type strain. The subject DNA is considered to have a function in conferring heat stress resistance to plants when the decrease in growth rate under high temperature growth conditions is smaller as compared to that of the wild type strain.

A DNA encoding a protein functionally equivalent to the Spl7 protein described in SEQ ID NO: 2 can be produced, for example, via methods well known to those skilled in the art. These methods include: methods using hybridization techniques (Southern, E. M. Journal of Molecular Biology, 98: 503, (1975)); and polymerase chain reaction (PCR) techniques (Saiki, R. K. et al. Science, 230: 1350-1354, (1985); Saiki, R. K. et al. Science, 239: 487-491, (1988)). It is routine for a person skilled in the art to isolate DNA with a high homology to the Spl7 gene from rice and other plants using the nucleotide sequence of the Spl7 gene (SEQ ID NO: 1) or parts thereof as a probe, and oligonucleotides hybridizing specifically to the nucleotide sequence of Spl7 gene as a primer. Such DNA encoding proteins functionally equivalent to the Spl7 protein, obtainable by hybridization techniques or PCR techniques, are included within the scope of the DNA of this invention.

Hybridization reactions to isolate such DNAs are preferably conducted under stringent conditions. Stringent hybridization conditions according to the present invention include conditions such as: 6 M urea, 0.4% SDS, and 0.5×SSC. DNAs with higher homology are expected when hybridization is performed under conditions with greater stringency, such as: 6 M urea, 0.4% SDS, and 0.1×SSC. The DNAs isolated under such conditions are expected to encode a protein having a high degree of amino acid homology with the Spl7 protein (SEQ ID NO: 2). As used herein, the phrase "high homology" through the entire amino acid sequence means an identity of at least 50% or more, preferably 70% or more, and most preferably 90% or more (e.g., 95% or more) The degree of sequence homology can be determined via programs of BLASTn (nucleotide level) and BLASTx (amino acid level) (Altschul et al. J. Mol. Biol. 215: 403-410, (1990)). These programs are based on the BLAST algorithm by Karlin and Altschul (Proc. Natl. Acad. Sci. USA, 87: 2264-2268, (1990) and Proc. Natl. Acad. Sci. USA, 90: 5873-5877, (1993)). To analyze a nucleotide sequences according to BLASTN, the parameters are set, for example, as score=100 and word length=12. On the other hand, the parameters used for the analysis of amino acid sequences by the BLASTX are set, for example, as score=50 and word length=3. Default parameters of each program are used when using BLAST and Gapped BLAST programs. Specific techniques for such analysis are known in the art.

The DNA of the present invention can be used, for example, to prepare recombinant proteins, to produce plant transformants with suppressed lesion formation or enhanced heat stress resistance, etc.

According to the present invention, a recombinant protein is generally prepared by inserting a DNA encoding a protein of the present invention into an appropriate expression vector, introducing the vector into an appropriate cell, culturing the transformed cells, allowing the cells to express the recombinant protein, and purifying the expressed protein. A recombinant protein can be expressed as a fusion protein with other proteins so as to be easily purified, for example, as a fusion protein with maltose binding protein in *Escherichia coli* (New England Biolabs, USA, vector pMAL series), as a fusion protein with glutathione-S-transferase (GST) (Amersham Pharmacia Biotech, vector pGEX series), or tagged with histidine (Novagen, pET series). The host cell is not limited to any particular type as long as the cell is suitable for expressing the recombinant protein. It is possible to utilize yeast, various animal, plant, or insect cells besides the above-described *E. coli*. A vector can be introduced into a host cell by a variety of methods known to one skilled in the art. For example, a transformation method using calcium ions (Mandel, M. and Higa, A. Journal of Molecular Biology, 53: 158-162 (1970), Hanahan, D. Journal of Molecular Biology, 166: 557-580 (1983)) can be used to introduce a vector into *E. coli*. A recombinant protein expressed in host cells can be purified and recovered from the host cells or the culture supernatant thereof via standard methods. When a recombinant protein is expressed as a fusion protein with maltose binding protein or other partners, the recombinant protein can be easily purified by affinity chromatography.

The resulting protein can be used to prepare an antibody that binds to the protein. For example, a polyclonal antibody can be prepared by immunizing animals (such as rabbits) with a purified protein or part thereof, of the present invention, followed by collecting blood from the animal after a certain period and removing the clots. A monoclonal antibody can be prepared by fusing myeloma cells with antibody-forming cells of animals immunized with the above protein or part thereof, isolating a monoclonal cell expressing a desired antibody (hybridoma), and recovering the antibody from said cell. The antibody produced by this method can be used to purify or detect a protein of the present invention.

Accordingly, another aspect of the present invention includes antibodies that bind to proteins of the invention.

A plant transformant with suppressed lesion formation or enhanced heat stress resistance can be created using DNAs of the present invention. More specifically, a DNA encoding a protein of the present invention is inserted into an appropriate vector; the vector is introduced into a plant cell; and the resulting transformed plant cell is regenerated.

Vectors used for the transformation of plant cells are not limited to any particular type as long as the vector can express inserted genes into plant cells. For example, vectors comprising promoters for constitutive gene expression in plant cells (e.g., cauliflower mosaic virus 35S promoter); and promoters inducible by exogenous stimuli can be used. The term "plant cell" used herein includes various forms of plant cells, such as cultured cell suspensions, protoplasts, leaf sections, and callus.

A vector can be introduced into plant cells by known methods, such as the polyethylene glycol method, electroporation; *Agrobacterium*-mediated transfer, and particle bombardment. Plants can be regenerated from transformed plant cells by known methods depending on the type of the plant cell (Toki et al., Plant Physiol. 100:1503-1507 (1995)). Some of the transformation and regeneration methods for rice plants include: (1) introducing genes into protoplasts using polyethylene glycol, and regenerating the plant body (suitable for indica rice cultivars) (Datta, S. K., in "Gene Transfer To Plants", Potrykus I and Spangenberg Eds., pp 66-74 (1995)); (2) introducing genes into protoplasts using electric pulse, and regenerating the plant body (suitable for japonica rice cultivars)(Toki et al., Plant Physiol. 100: 1503-1507 (1992)); (3) introducing genes directly into cells by particle bombardment and regenerating the plant body (Christou et al., Bio/Technology, 9: 957-962 (1991)); (4) introducing genes using *Agrobacterium*, and regenerating the plant body (Hiei et al., Plant J. 6: 271-282 (1994)). These methods are well established in the art and are widely used in the technical field of the present invention. These methods can be suitably used in the present invention.

Once a transformed plant, with the DNA of the present invention is introduced into the genome, is obtained, it is possible to obtain descendants from that plant body by sexual or vegetative propagation. Alternatively, plants can be mass-produced from breeding materials (for example, seeds, fruits, ears, tubers, tubercles, tubs, callus, protoplast, etc.) obtained from the plant, as well as descendants or clones thereof. Plant cells transformed with the DNA of the present invention, plant bodies including these cells, descendants and clones of the plant, as well as breeding material obtained from the plant, its descendant and clones, are all included within the scope of the present invention.

Plants produced above have enhanced heat stress resistance and suppressed lesion formation compared to wild type plants. Employing the method of the present invention, productivity of valuable crops like rice can be increased which is greatly beneficial.

Furthermore, the present invention provides polynucleotides comprising at least 15 nucleotides that are complementary to a DNA of the present invention consisting of the nucleotide sequence of SEQ ID NO: 1 or to the complementary strand thereof. The term "complementary strand," as used herein, refers to one strand of a double stranded DNA composed of A:T and G:C base pairs. In addition, "complementary," as used herein, refers to not only those completely matching within a region of at least 15 continuous nucleotides, but also those having a homology of at least 70%, preferably at least 80%, more preferably 90%, and most preferably 95% or higher within that region. Such DNAs are useful as probes to detect or isolate a DNA of the present invention, or as primers to amplify a DNA of the present invention.

BEST MODE FOR CARRYING OUT THE INVENTION

The present invention is specifically illustrated below with reference to Examples, but it is not to be construed as being limited thereto.

EXAMPLE 1

Construction of a Genetic Map

Fine scale linkage analysis of Spl7 region essential for map base cloning was conducted using a large scale segregating population. 298 individuals of the F2 population obtained by crossing Spl7 mutant strain with SL18 were used as the population for linkage analysis. SL18 has a genetic background of and Nipponbare, and its chromosome 5 is substituted with that of Kasalath. According to a linkage analysis using RFLP markers, the Spl7 locus was found to exist between RFLP marker S869 and R2781, and to be cosegregated with C11368, S2581, S1762, S1831, and B344 (FIG. 2A).

Furthermore, 2646 individuals of the, F2 population were used for linkage analysis to construct a fine scale genetic map of the Spl7 region. CAPS (Cleaved Amplified Polymorphic Sequence) markers were used for efficient analysis procedures. More specifically, plants with chromosome recombination adjacent to Spl7 were screened in the F2 population using CAPS markers S869 and R2781, each marker adjacent to Spl7. Accordingly, 65 recombinants could be selected (FIG. 2B) Using these recombinants, a fine scale linkage map was constructed with RFLP markers constructed as described below.

EXAMPLE 2

Alignment of the Spl7 Gene Region Using Yeast Artificial Chromosome (YAC) Clones and P1 Derived Artificial Chromosome (PAC) Clones YAC clones comprising the nucleotide sequence of DNA markers, S869, C11368, S2581, and R2781, existing adjacent to the Spl7 locus were specified using the alignment map of Nipponbare YAC clones constructed in the Rice Genome Research Program (FIG. 2C). Additionally, end fragments of the specified YAC clones, Y4666, Y2205, Y3824c, Y6089, and Y2288, were isolated by the cassette method to align the specified YAC clones. The results revealed that the YAC clone Y4666, Y2205, and Y3824c comprised the Spl7 gene region (FIG. 2C).

Furthermore, to delimit the candidate region for the Spl7Spl7 gene, STS primer set (primers 5'-GACCTGT-GCTCTGCCTTTCT-3'/SEQ ID NO: 3 and 5'-GTATGC-CAACTGCTCMCTT-3'/SEQ ID NO: 4; amplified genomic fragment of 0.4 kb), prepared from the RFLP marker C11368 existing on the same position as the Spl7 locus, was used for screening the Nipponbare PAC clone library (mean insert length of 112 kb; 18432 clones; about 4.5 times of the rice genome) constructed in the Rice Genome Research Program (Baba et al., Bull. Natl. Inst. Agrobiol. Resour. 14: 24-36 (2000)). As a result, 9 PAC clones were selected. By aligning these PAC clones, 8 PAC clones, represented by P0029H1, were shown to contain the Spl7 locus (FIG. 2D).

EXAMPLE 3

Delimitation of the Spl7 Gene Region

Figure 1:
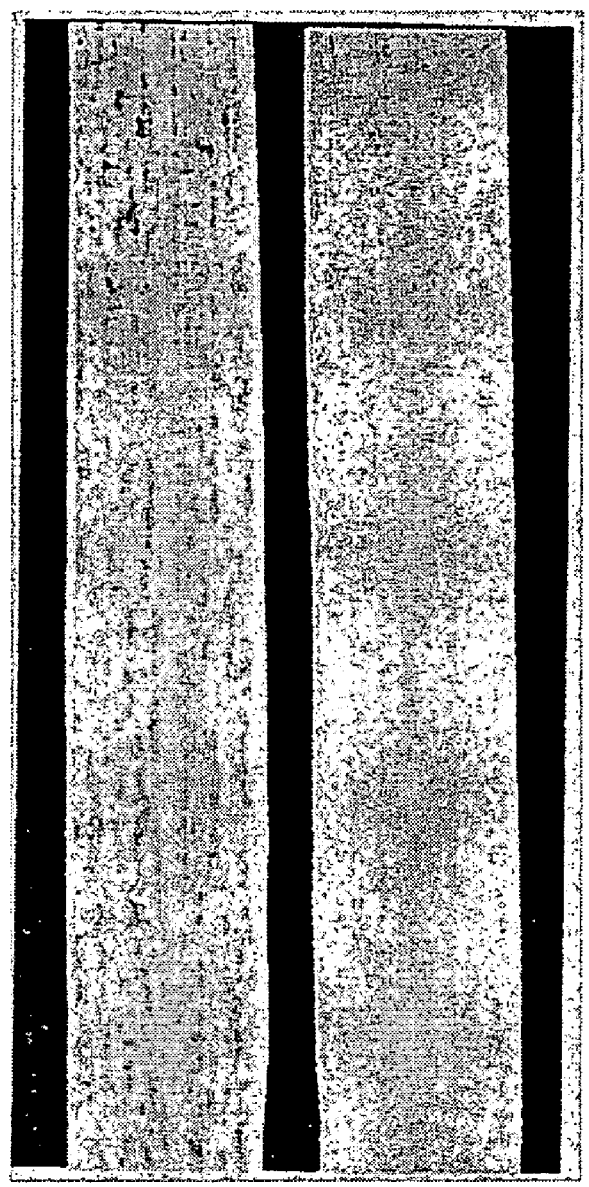
FIG. 1 depicts photographs of a leaf of the spl7 mutant KL210 (left panel) and a leaf of the Nipponbare (right panel).
Figure 2:
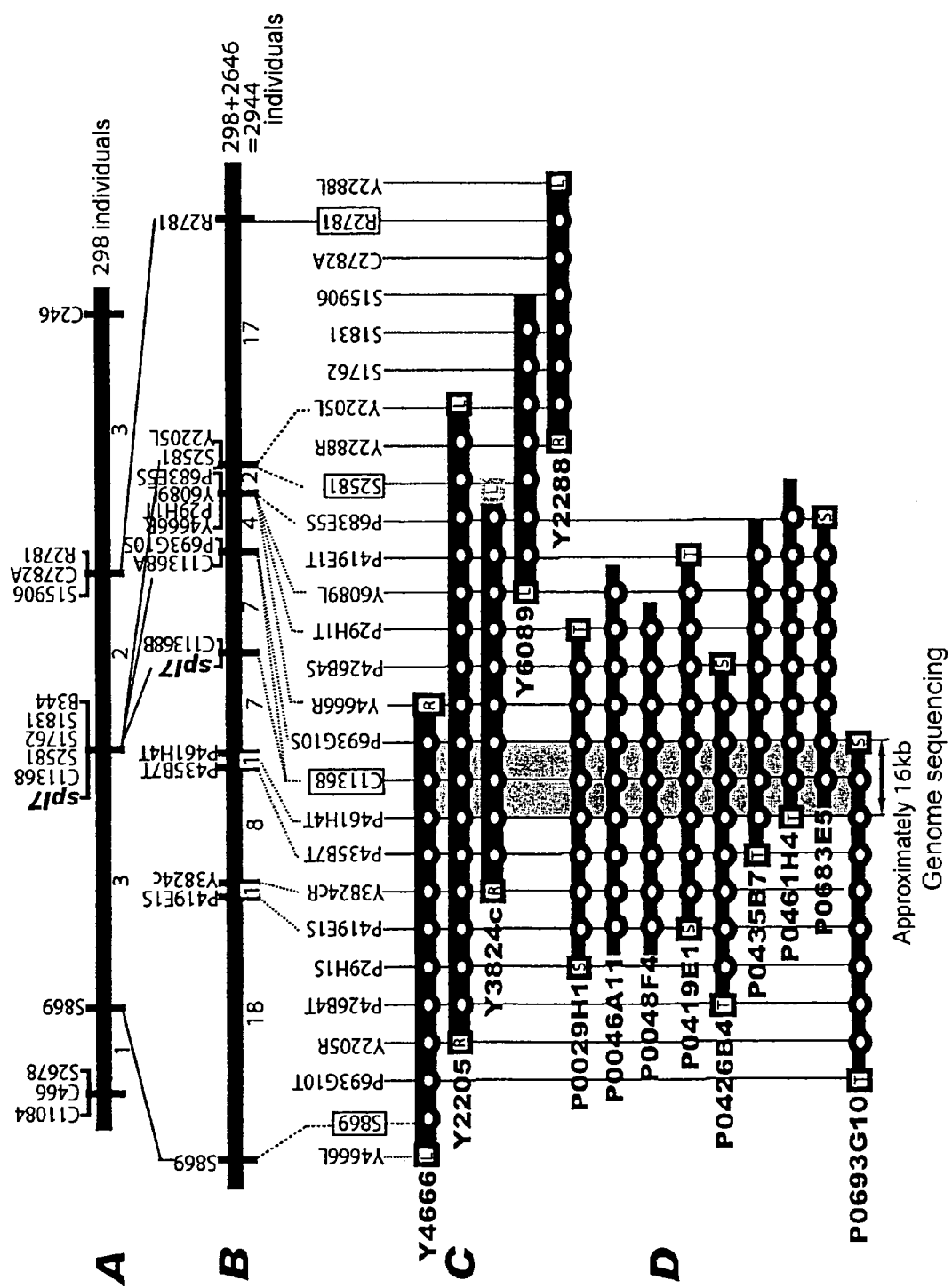
FIG. 2 shows a fine scale linkage map of the Spl7 gene region and an alignment map of genomic clones. A and B represent genetic maps constructed from a segregating population of 298 individuals and 2944 individuals, respectively. C and D represent alignment maps constructed from YAC and PAC clones of Nipponbare, respectively.

The end fragments of YAC and PAC clones aligned within the Spl7 region were cloned and used as new RFLP or CAPS markers for constructing a fine scale genetic map. The result revealed that the Spl7 locus is located on a genomic region between RFLP markers P461H4T and P693G10S and is cosegregated with RFLP marker C11368B. Accordingly, the Spl7 locus was demonstrated to exist on a genomic region of about 16 kb between the 2 markers (FIG. 2).

EXAMPLE 4

Identification of the Candidate Genomic Region by Nucleotide Sequence Analysis

The genomic candidate region of 16 kb in the PAC clone P0029H1, which is expected to contain the Spl7 gene, was subjected to nucleotide sequence analysis. The nucleotide sequence was analyzed by subcloning the candidate region first with restriction enzymes Not I and Sal I, then with various other restriction enzymes, followed by the dye-primer method. CAPS markers were newly constructed using the nucleotide sequence information of the candidate gene region, which was determined by the linkage analysis, to further delimit the candidate region. The Spl7 gene cosegregated with the CAPS marker HsfC2-1 (primers 5'-TCTCTCTCGTTCGTTCCCCG-3'/SEQ ID NO: 5 and 5'-TGGATAAATGGAGATGGGCA-3'/SEQ ID NO: 6; restriction enzyme Apa I), and 3 and 7 recombinants, respectively, at S12C6-6d (primers 5'-TCGGCATCGGC-TATTATCGG-3'/SEQ ID NO: 7 and 5'-GATTTCGG-GATACTGTGCGT/SEQ ID NO: 8; restriction enzyme NIa III) and HsfC3-3' (primers 5'-ACGATGTGTTTTGG-GAGCGG-3'/SEQ ID NO: 9 and 5'-GACCTGTGCTCTGC-CTTTCT-3'/SEQ ID NO: 10; restriction enzyme NIa III) were identified.

Figure 3:
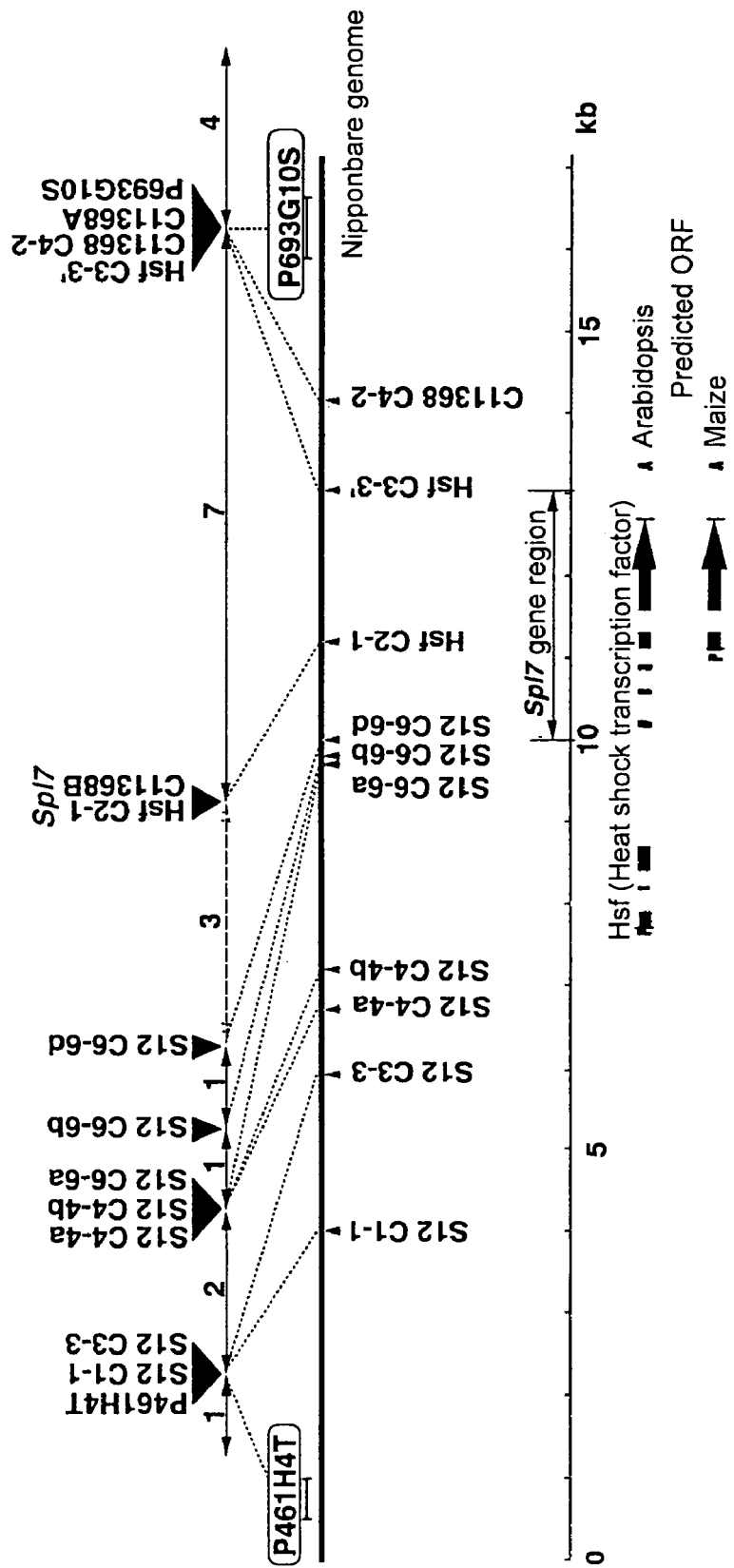
FIG. 3 shows a fine scale genetic map of the Spl7 gene region, and a map indicating candidate genomic region and the predicted gene thereon.

Thus, the Spl7 gene was shown to exist on a genomic region of about 3 kb between the CAPS markers S12C6-6d and HsfC3-3' (FIG. 3). Furthermore, gene prediction and similarity search was conducted against the nucleotide sequence of the candidate genomic region, predicting only a gene, that has similar nucleotide sequence with the Hsf gene that is isolated from plants such as tomato and *Arabidopsis* (FIG. 3). The Hsf gene is shown to function as a transcription-regulating factor of a heat shock induced protein.

EXAMPLE 5

Nucleotide Sequence Analysis of the Spl7 Candidate Gene

Figure 4:
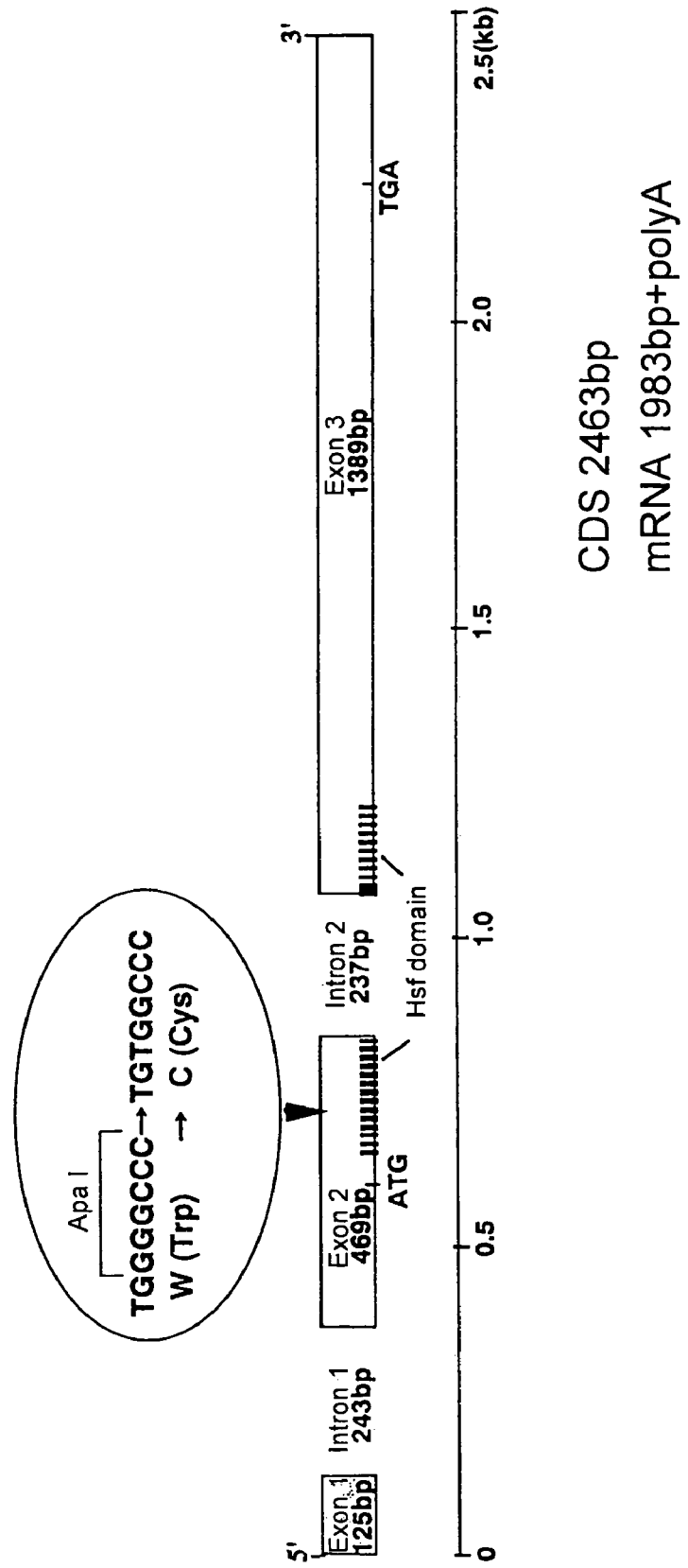
FIG. 4 illustrates the structure of the Spl7 candidate gene and compares the genomic nucleotide sequence of Nipponbare with that of KL210.

Using the Hsf like gene as the candidate for the Spl7 gene, the nucleotide sequence of corresponding region in mutant strain KL210 was determined. Specifically, the nucleotide sequence analysis was conducted by cloning products of genomic PCR and RT-PCR using primers designed to amplify the corresponding nucleotides based on the already obtained nucleotide sequence information of Nipponbare. A substitution of a nucleotide could be detected by comparing the nucleotide sequence of the wild type and those of mutant genes. As predicted, the nucleotide substitution results in a substitution of tryptophan to cystein (FIG. 4). The substituted amino acid is a part of amino acids highly conserved in the Hsf gene. Thus, the amino acid substitution is considered to be the cause of the loss or decrease in the Spl7 protein function in mutant strains.

EXAMPLE 6

Verification of the Candidate Gene Function by Transformation

The 5.6 kb Nsp V-Bgl III, Nipponbare genomic region fragment, comprising the predicted 5' upstream promoter region specified as the candidate for Spl7 gene, was inserted into vector pPZP2H-lac so that it could be used for transformation via *Agrobacterium*. Transformation was performed according to the method of Toki (Plant Mol. Biol. Rep. 15: 16-21 (1997)) using either the vector #178, inserted with the fragment, or the vector alone. Spl7 mutant strain KL210 was used as the strain for transformation. 150 and 50 of hygromycine resistant individuals, respectively, were obtained by the transformation experiment using the 5.6 kb Nsp V-Bgl II fragment and the vector alone. The integration of the candidate gene was confirmed by PCR method using candidate gene specific primers (sense strand 5'-GTCTC-CGTGGCCGTGGCTGA-3'/SEQ ID NO: 11 and antisense strand 5'-AACGAGGMTCTTAGAAGGG-3'/SEQ ID NO: 12).

Figure 5:
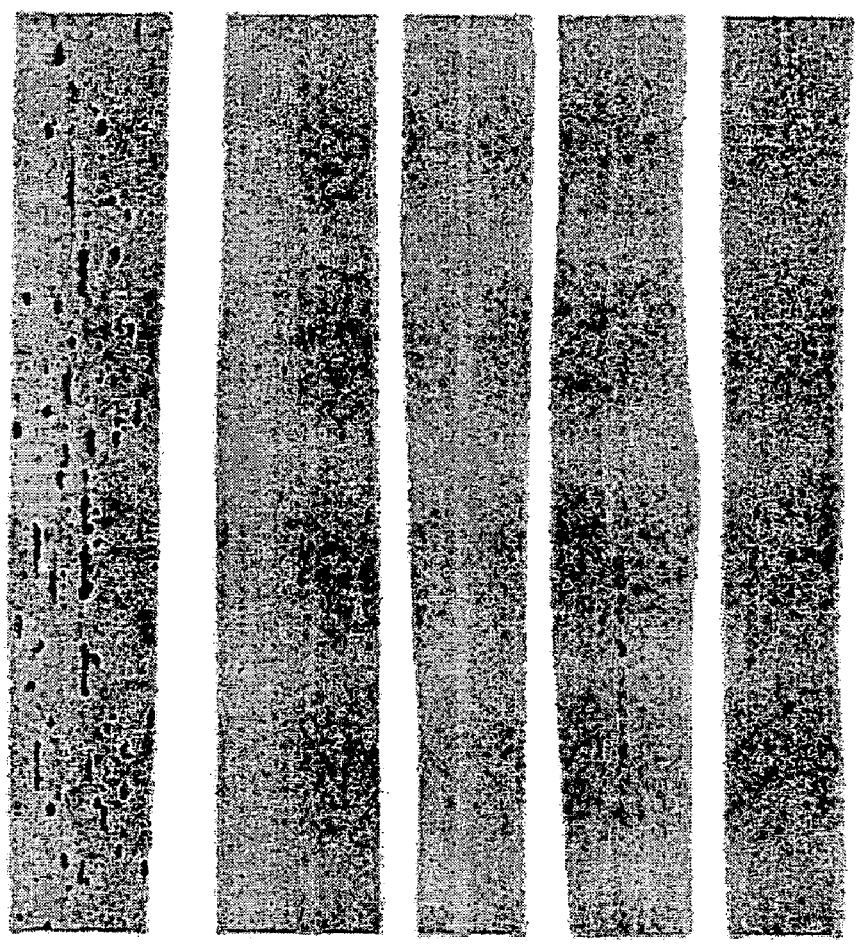
FIG. 5 is photographs of a leaf of the spl7 mutant KL210 (left panel) and a leaf of the transformant (4 panels on the right).

The result revealed that all 150 transformants contained the candidate gene. The transformants were grown in an isolated green house under natural day length condition (transferred into an isolated green house (Tsukuba) from a growth chamber in March) to investigate the formation of lesions. As a result, the plant transformed with the vector alone formed lesions at the late stage of growth similar to the mutant strain KL210, whereas no lesion formation was observed on any plant where the candidate gene was introduced (FIG. 5). Furthermore, lesions were formed on 6 plants and none were formed on the 18 plants out of the 24 self-pollinated progenies, which were expected to be transformed only with one copy of the transgene. The resulting segregation ratio fitted to an expected rate of 1:3. These results demonstrate that the function of the candidate gene region (Nsp V-Bgl II of 5.6 kb) is to suppress lesion formation on the mutant strain, KL210, and also that the candidate gene is the Spl7 gene.

EXAMPLE 7

Conditions Necessary for Lesion Formation

Figure 6:
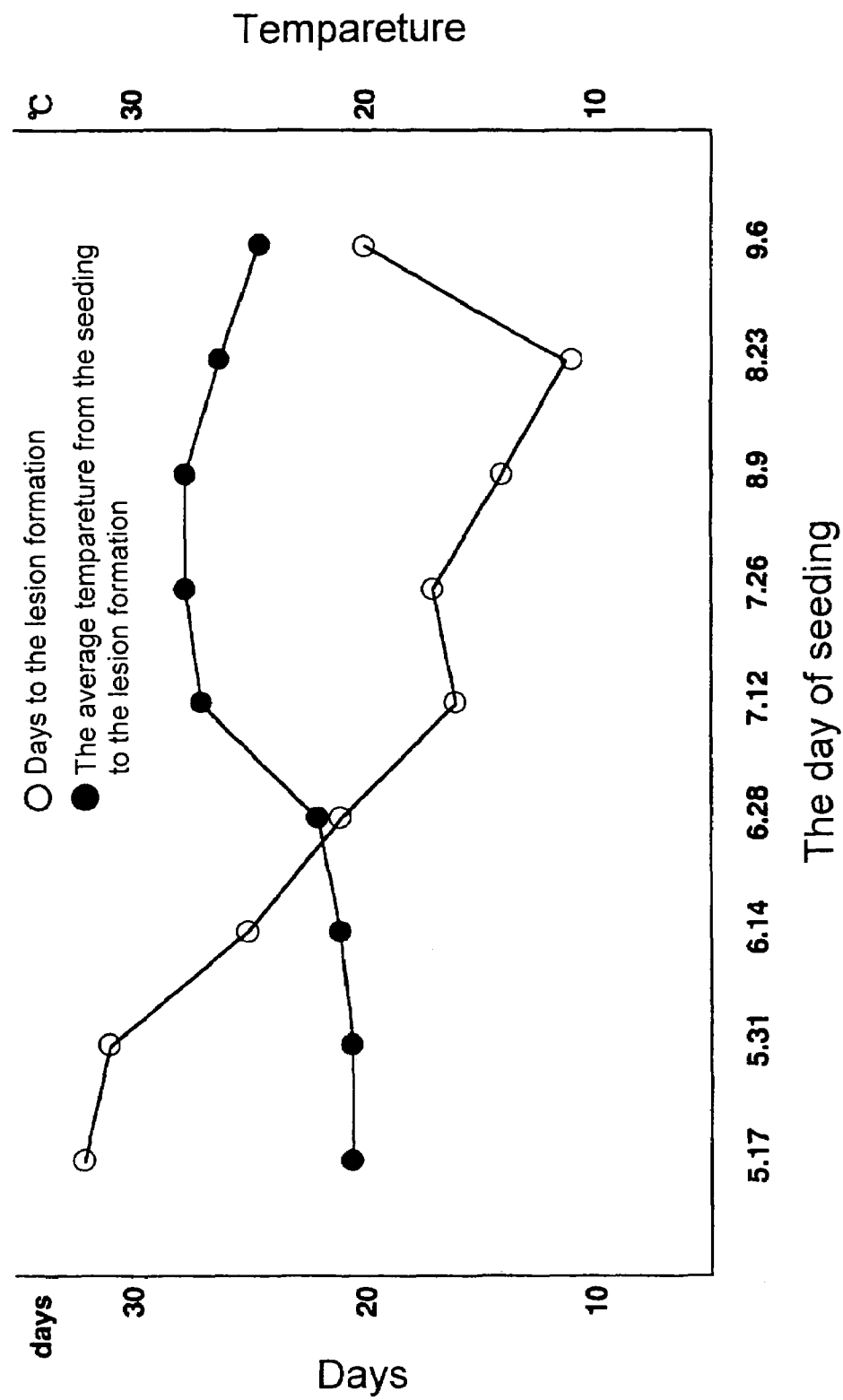
FIG. 6 represents the relationship between days required for lesion formation on spl7 mutants and mean temperature under natural growth conditions.

The days required for lesion formation on Spl7 mutant strain KL210 were investigated by seeding KL210 and Nipponbare having the wild type gene at an interval of 14 days starting May 17, 1999. The days required for lesion formation decreased for plants seeded till August 23, and increased for those seeded on September 6 (FIG. 6). On the other hand, the mean temperature from seeding to lesion formation increased until August 9 and decreased thereafter (FIG. 6). The shortest time till lesion formation was 11 days for those seeded on August 23, when even the mean temperature had declined. However, the highest temperature of 36° C. in 1999 was recorded shortly before lesion formation. More days (more than 60 days after seeding) are needed for lesion formation on plants grown in growth chambers in winter. Furthermore, the degree of lesion formation was also suppressed in winter. Moreover, when plants were grown in a growth chamber where the temperature was 26° C. or less, lesions did not appear during any growth period, whereas lesions appeared after a month in a growth chamber where the temperature was 37° C. According to these results, it was suggested that high temperature is essential for lesion formation to some extent, and additionally, that high temperature enhances lesion formation.

Figure 7:
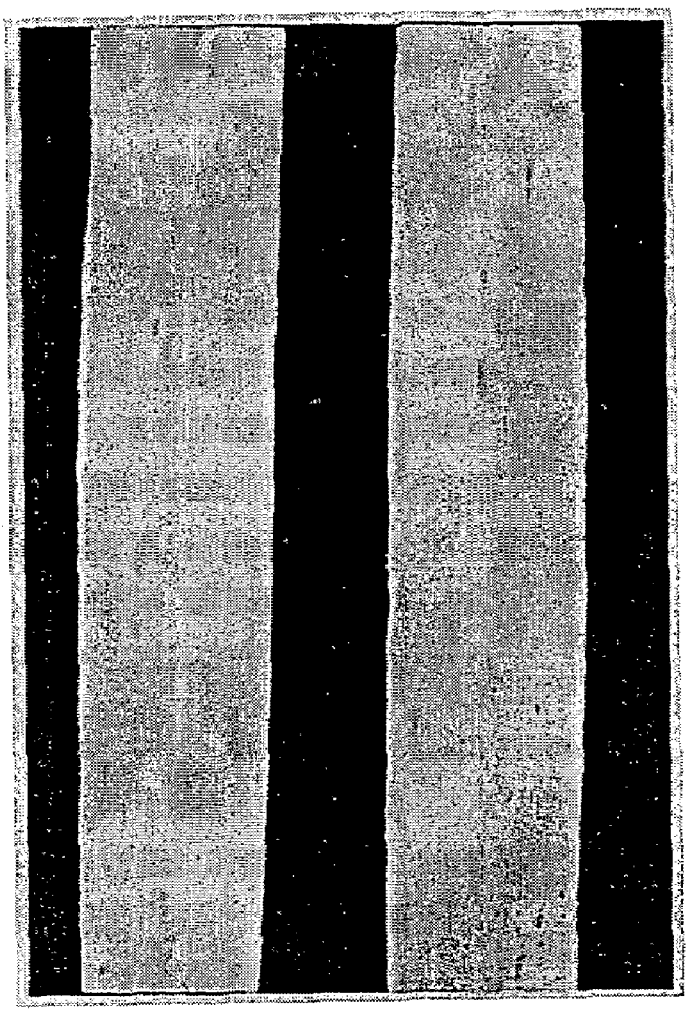
FIG. 7 is photographs of a leaf of spl7 mutant KL210 grown by blocking ultraviolet rays (left panel) and a leaf grown without blocking ultraviolet rays (right panel).

Next, KL210 and Nipponbare were grown by covering them with sheets that blocked ultraviolet rays or with plastic sheets which do not block UVs. Whatever sheet KL210 was grown covered with, lesion formation was observed on the 25th day from seeding. However, the degree of lesion formation was suppressed on plants that were blocked from UV irradiation as compared to those where UV was allowed through (FIG. 7). These results demonstrate that UV irradiation is one of the conditions required for enhancing lesion formation.

According to the results obtained above, it was concluded that the Hsf like gene is the Spl7 gene candidate. Then by the map base cloning method it was established to be the Spl7 gene, that the gene which suppresses lesion formation on rice. Hence, the biological function of Hsf like genes in plants was demonstrated for the first time in the present invention.

INDUSTRIAL APPLICABILITY

Tropical plants, for example, rice, are adapted to a certain degree of high temperature compared to barley, and hence acquire resistance against heat stress. However, the growth temperature of plants is climbing higher due to global warming. Under such conditions, methods to efficiently confer heat stress resistance to plants have been desired for stabilizing crop production in the future. Many points in the mechanism of heat stress resistance remain unexplained and no efficient method for positively enhancing resistance by modification has been known. By effectively conferring heat stress resistance to plants, not only stable food production at today's level's will be maintained in spite of global warming, but cultivation of crops in regions where it was unable to grow plants will also be possible. The Spl7 gene of the present invention enhances heat stress resistance in plants and has a function in suppressing lesion formation on plants. Hence, the Spl7 gene of the present invention greatly contributes to the above-mentioned objectives.

The invention claimed is:

1. An isolated DNA encoding a protein derived from plants that enhances the heat stress resistance of plants, said DNA is selected from the group consisting of:
   (a) DNA encoding a protein comprising the amino acid sequence of SEQ ID NO: 2;
   (b) a DNA including the coding region of the nucleotide sequence of SEQ ID NO: 1;
   (c) a DNA encoding a protein comprising an amino acid sequence having at least 95% sequence identity with SEQ ID NO: 2; and
   (d) a DNA comprising a nucleotide sequence having 90% identity to the coding region of SEQ ID NO: 1.

2. A vector comprising the DNA of claim 1.

3. A transformed cell comprising the DNA of claim 1.

4. The transformed cell of claim 3, wherein said transformed cell is a plant cell.

5. A plant transformant comprising the transformed cell of claim 3, or the progeny thereof comprising the DNA of claim 1.

6. The plant transformant of claim 5, wherein said progeny is a clone.

7. A breeding material of the plant transformant of claim 5.

* * * * *